(12) United States Patent
Giordana

(10) Patent No.: US 11,944,565 B2
(45) Date of Patent: Apr. 2, 2024

(54) FINGER SPLINT FOR PIP IMMOBILIZATION

(71) Applicant: Jacob Giordana, Hudson, WI (US)

(72) Inventor: Jacob Giordana, Hudson, WI (US)

(73) Assignee: Jacob Giordana, Hudson, WI (US)

( * ) Notice: Subject to any disclaimer, the term of this patent is extended or adjusted under 35 U.S.C. 154(b) by 0 days.

(21) Appl. No.: 16/815,422

(22) Filed: Mar. 11, 2020

(65) Prior Publication Data

US 2021/0282958 A1 Sep. 16, 2021

(51) Int. Cl.
*A61F 5/058* (2006.01)

(52) U.S. Cl.
CPC ................................ *A61F 5/05875* (2013.01)

(58) Field of Classification Search
CPC .. A61F 13/063104; A61F 13/105; A61F 5/01;
A61F 5/013; A61F 5/05866; A61F
5/05875; A61F 5/0118; A61F 5/04; A61F
5/10; A61F 5/50; A61F 5/0127; A61F
2/586; A61F 2/54; A61F 2/58; A61F
2002/587; A61H 1/02
USPC ....... 602/5, 12, 15, 21, 22; 128/880; 623/59,
623/60, 62, 63, 54, 65; 482/47, 48
See application file for complete search history.

(56) References Cited

U.S. PATENT DOCUMENTS

| | | | | |
|---|---|---|---|---|
| 1,585,861 A | * | 5/1926 | Huff ........................ | A61F 5/41 600/39 |
| 1,913,463 A | * | 6/1933 | Toelcke ................... | A44C 9/00 63/15 |
| 4,043,145 A | * | 8/1977 | Chervin ................... | A44C 9/00 63/15 |
| 4,657,000 A | * | 4/1987 | Hepburn ............... | A61F 5/0102 602/16 |
| 4,944,290 A | * | 7/1990 | Hepburn ............. | A61F 5/05875 602/22 |

(Continued)

FOREIGN PATENT DOCUMENTS

| CN | 1060398 A | * | 4/1992 |
| CN | 207545735 U | * | 6/2018 |

(Continued)

OTHER PUBLICATIONS

Saunders et al. (Hand and Upper Extremity Rehabilitation A Practical Guide Fourth Edition, Elsevier, Dec. 3, 2015) (Year: 2015).*

*Primary Examiner* — Ophelia A Hawthorne
*Assistant Examiner* — Michael Milo
(74) *Attorney, Agent, or Firm* — Schwegman Lundberg & Woessner, P.A.

(57) ABSTRACT

A splint immobilizes a proximal interphalangeal (PIP) joint of a finger while allowing a distal interphalangeal (DIP) joint to be flexed. The splint may include a splint body and straps configured to secure the splint body to the finger. The splint body may have a size to fit the finger, a shape to generally conform to and partially surround the finger from the palmar side, and a length to extend from a proximal phalanx of the finger across the PIP joint to a middle phalanx of the finger without extending across the DIP joint. The splint body may have an integrally-formed periphery defining a central opening. The periphery may include a first base at the proximal phalanx, a second base at the middle phalanx, and opposing sides extending between the first and second bases.

19 Claims, 3 Drawing Sheets

(56) References Cited

U.S. PATENT DOCUMENTS

| | | | | |
|---|---|---|---|---|
| 5,848,983 | A * | 12/1998 | Basaj | A61F 5/05866 |
| | | | | 602/5 |
| 5,921,945 | A * | 7/1999 | Gray | A61F 5/05866 |
| | | | | 602/5 |
| 5,947,915 | A * | 9/1999 | Thibodo, Jr. | A61F 5/05875 |
| | | | | 602/5 |
| 6,575,925 | B1 * | 6/2003 | Noble | A61F 5/05875 |
| | | | | 602/20 |
| 2004/0002673 | A1 * | 1/2004 | Ferraioli | A61F 5/05875 |
| | | | | 602/22 |
| 2010/0137769 | A1 * | 6/2010 | Schulte | A61F 5/05875 |
| | | | | 602/22 |
| 2010/0262057 | A1 * | 10/2010 | Chandrasekar | A61F 5/10 |
| | | | | 602/22 |
| 2016/0313798 | A1 * | 10/2016 | Connor | G06F 3/017 |
| 2018/0250153 | A1 * | 9/2018 | Kleynhans | A61F 5/05875 |
| 2018/0343990 | A1 * | 12/2018 | Repossi | A44C 9/0015 |
| 2018/0368491 | A1 * | 12/2018 | Anunike | A63B 71/14 |
| 2019/0314542 | A1 * | 10/2019 | Ish Cassit | A61F 5/0104 |

FOREIGN PATENT DOCUMENTS

| | | | | |
|---|---|---|---|---|
| DE | 202012010235 | U1 * | 1/2013 | A61F 13/068 |
| DE | 202012010235 | U1 * | 3/2013 | A61F 13/068 |
| EP | 1378217 | A1 * | 1/2004 | A61F 5/0118 |
| EP | 2087863 | A1 * | 8/2009 | A61F 5/0118 |
| EP | 2873374 | A1 * | 5/2015 | A41D 13/087 |
| ES | 2284412 | A1 * | 11/2007 | A61F 5/0118 |
| FR | 2836824 | A1 * | 9/2003 | A61F 5/05875 |
| WO | WO-2004021936 | A1 * | 3/2004 | A61F 2/54 |
| WO | WO-2017055858 | A1 * | 4/2017 | A61F 5/05866 |

\* cited by examiner

FINGER SPLINT FOR PIP IMMOBILIZATION

TECHNICAL FIELD

This document relates generally to medical devices, and more particularly, but not by way of limitation, to splints designed to immobilize the PIP joint.

BACKGROUND

Injured fingers may be immobilized using a splint. For example, handmade splints have been created using aluminum and athletic tape. Such splints may have deficiencies. For example, such splints may be difficult to apply to the injured finger, may cause necrosis, may be too weak to hold the injured finger in a desired position, and may prevent partial functionality of the splinted finger.

SUMMARY

This document discusses, among other things, a splint for immobilizing a proximal interphalangeal (PIP) joint of a finger while allowing both a distal interphalangeal (DIP) joint and the metacarpophalangeal (MCP) joint of the finger to be flexed. The splint may include a splint body and straps configured to wrap around a dorsal side of the finger to secure the splint body to the finger.

The splint body may have a size to fit the finger, and a shape to generally conform to and partially surround the finger from a palmar side of the finger. The splint body may have a width to partially surround the finger and a length to extend from a proximal phalanx of the finger across the PIP joint to a middle phalanx of the finger, wherein the length does not extend across the DIP joint. The splint body may have a central opening and an integrally-formed periphery defining central opening of the splint body. The integrally-formed periphery may include a first base configured to partially surround the finger from the palmar side at the proximal phalanx of the finger, a second base configured to partially surround the finger from the palmar side at the middle phalanx of the finger, and opposing sides that are generally straight extending between the first and second bases and configured for placement on opposing sides of the finger.

The straps may include at least a first strap attached to the first base and configured for use to wrap around the proximal phalanx of the finger, at least a second strap attached to the second base and configured for use to wrap around the middle phalanx of the finger; and at least a third strap attached to at least one of the opposing sides between the first base and the second base, and configured for use to wrap around the finger. The third strap may be positioned over the PIP joint to help immobilize the PIP joint.

A method for immobilizing a proximal interphalangeal (PIP) joint of a finger may comprise attaching a splint to a finger. The splint may include a splint body having a size to fit the finger and straps. The splint body may have a shape to generally conform to and partially surround the finger from a palmar side of the finger. The splint body may have a width to partially surround the finger and have a length to extend from a proximal phalanx of the finger across the PIP joint to a middle phalanx of the finger without extending across the DIP joint. The splint body may have an integrally-formed periphery defining a central opening of the splint body. The integrally-formed periphery may include a first base configured to partially surround the finger from the palmar side at the proximal phalanx of the finger, a second base configured to partially surround the finger from the palmar side at the middle phalanx of the finger, and opposing sides that are generally straight extending between the first and second bases and configured for placement on opposing sides of the finger.

Attaching the splint to the finger may include wrapping at least a first strap attached to the first base around the proximal phalanx of the finger, wrapping at least a second strap attached to the second base around the middle phalanx of the finger, and wrapping at least a third strap attached to at least one of the opposing sides around the finger. The third strap may be positioned over the PIP joint to help immobilize the PIP joint.

The splint may be used to treat a Boutonniere deformity, as it allows a patient to flex the distal interphalangeal (DIP) joint of the finger when the splint body is attached to the finger.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
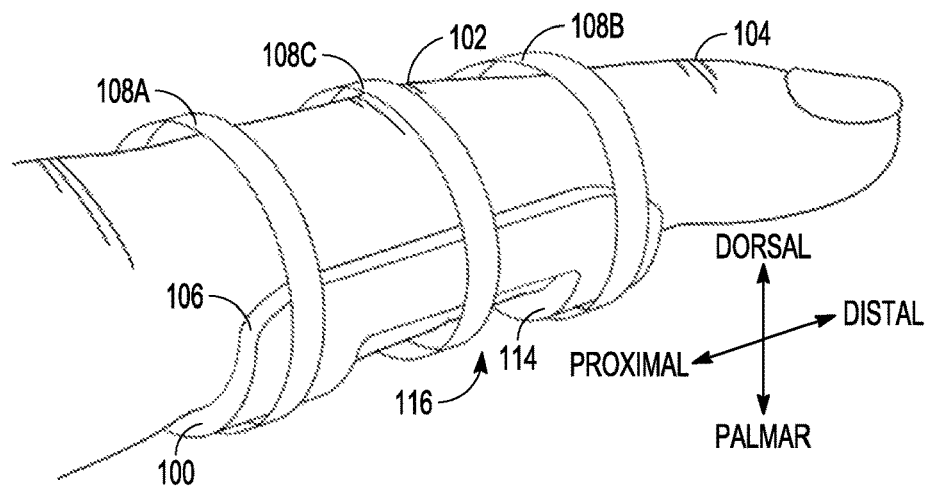
FIGS. 1A-1C illustrate a perspective view, a side view, and an end view of an embodiment of a splint on a finger.

This document discusses, among other things, a splint for immobilizing a proximal interphalangeal (PIP) joint of a finger while allowing a distal interphalangeal (DIP) joint of the finger to be flexed. An overview of some improved features is provided below, followed by a more detailed description of these features with reference to the drawings.

The disclosed splint was developed after the inventor was injured when sliding headfirst into a base during a baseball game. The headfirst slide jammed a finger and injured the central slip tendon causing a boutonniere deformity (an injury in which the finger is stuck in a Z-shape where the PIP joint is stuck flexed towards the palm while the DIP joint is stuck flexed away from the palm). A boutonniere deformity results when the tendons (e.g. central slip tendon that runs on the top or dorsal side of the finger and attaches to the middle bone, referred to as the middle phalanx, of the finger) that normally straighten the middle joint of the finger are injured. This deformity may develop from arthritis, or may develop after trauma, such as a cut to the central slip tendon or a blow to a flexed finger. Flexion at the PIP joint (the joint nearest the knuckle is bent toward the palm) and hyperextension at the DIP joint (the farthest joint is bent back away from the palm).

The deformity must be treated early to retain the range of motion of the finger. This deformity may be surgically treated or non-surgically treated using a splint to straighten and immobilize the finger. The splint may need to be worn continuously for weeks (e.g. 6 weeks) after which it may still need to be worn intermittently (e.g. at night). Exercises may be prescribed to strengthen the finger, increase range of motion and flexibility. The exercises may include repeatedly raising and lowering the finger at the knuckle (metacarpophalangeal joint or MCP) and repeatedly bending and straightening the fingertip.

Boutonniere deformities do not heal on their own over a few days or weeks. Some deformities do not heal. A hand specialist informed the inventor that he had not seen much success with healing this specific injury and indicated that the injury may be with him for the rest of his life. Injuries to the central slip (tendon) often need PIP joint immobilization to heal. Injuries that severed a central slip require PIP immobilization while enabling the fingertip to be straightened at the DIP joint to allow for tendon regrowth. If the central slip tendon is not severed, then, in order to allow tendon realignment, the treatment should allow full function of the DIP and immobilization of the PIP. A common practice is making a splint with aluminum and padding, and securing it to the finger with athletic tape. The hand specialist provided the inventor with a handmade splint comprised of aluminum and athletic tape. However, the frame could be bent in half with the pinky finger.

The inventor fabricated a split that immobilized the PIP joint and allowed full DIP functionality from an altered plastic butter knife. The finger had healed and was fully functional after six weeks of wearing the initial splint. However, the initial splint had was causing necrotic tissue due to oxygen deprivation. The splint disclosed herein has a hollow area to allow for oxygen to reach the finger to avoid the issue of necrotic tissue. Some embodiments of the splint further have perforations or additional apertures throughout the structure to promote breathability and discourage necrosis.

In addition to boutonniere deformities, a PIP immobilization splint such as disclosed herein may be useful to treat other PIP injuries such as dislocations, subluxations, fractures, or other injuries that impact the PIP joint.

Figure 1B:
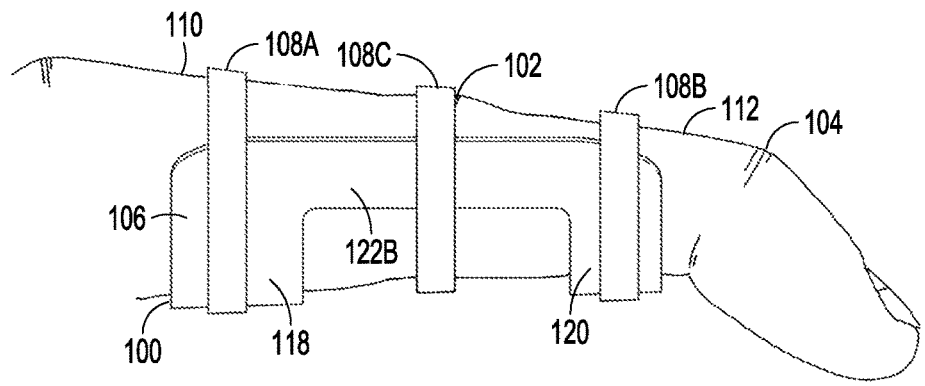
Figure 1C:
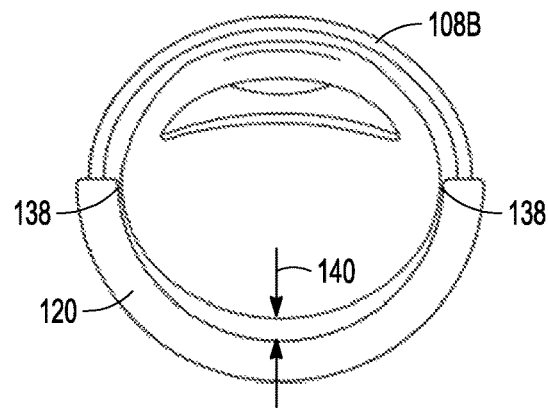
Figure 2A:
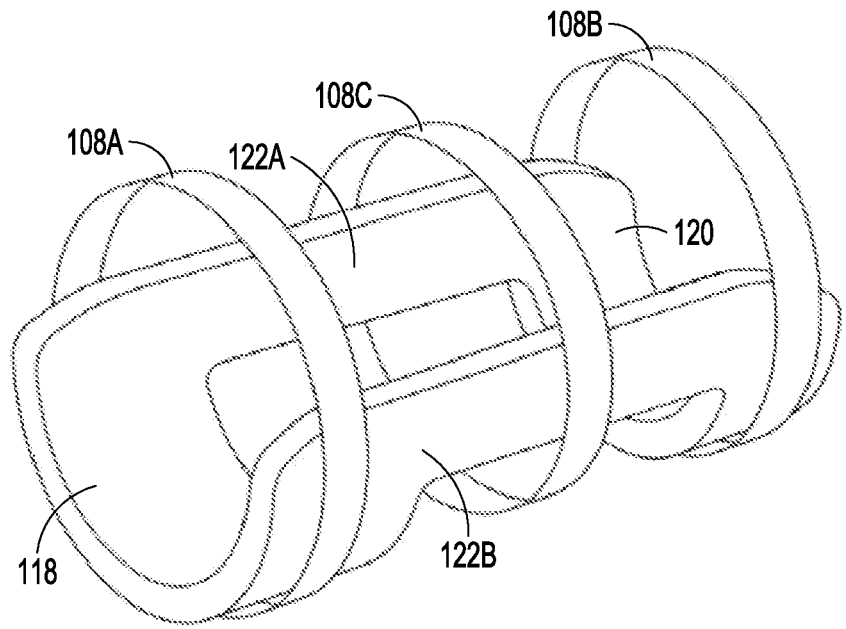
FIGS. 2A-2D illustrate a perspective view, a top view, an end view, and a side view of an embodiment of the splint.
Figure 2B:
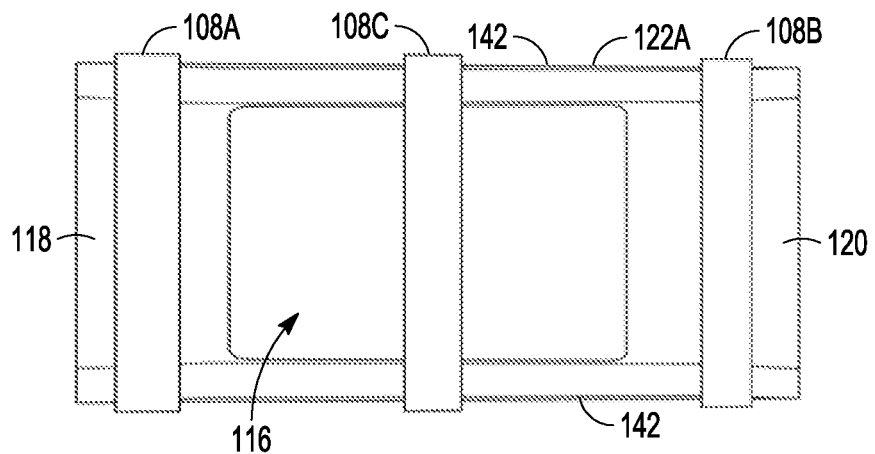
Figure 2C:
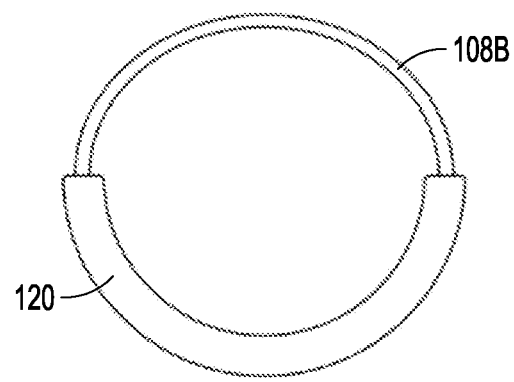
Figure 2D:
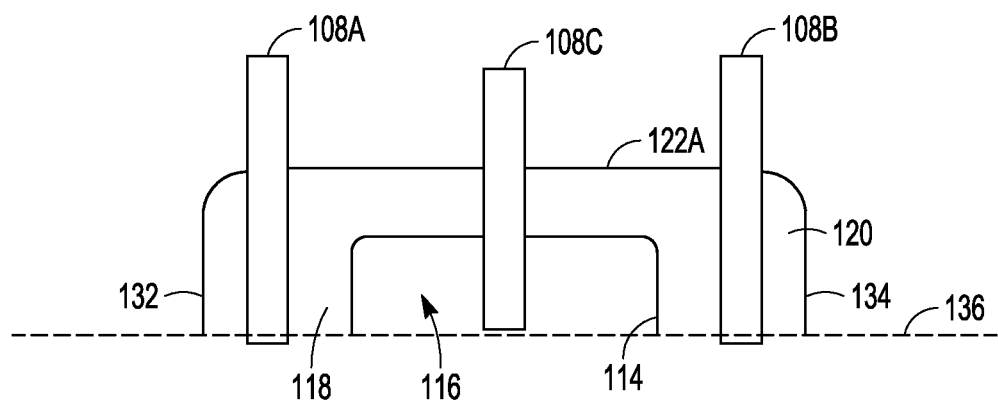

FIGS. 1A-1C illustrate a perspective view, a side view, and an end view of an embodiment of a splint on a finger; and FIGS. 2A-2D illustrate a perspective view, a top view, an end view, and a side view of an embodiment of the splint. The illustrated splint 100 is configured to immobilize a PIP joint 102 of a finger while allowing a DIP joint 104 of the finger to be flexed. The illustrated splint 100 includes a splint body 106 and straps 108A, 108B and 108C for securing the splint body 106 to the finger.

The splint body 106 has a size to fit the finger to be treated. Different sizes, such as by way of example and not limitation small, medium, large, and extra-large, may be used for different youth and adult sizes similar to glove sizes. The splint body 106 has a shape to generally conform to and partially surround the finger from a palmar side of the finger. The splint body 106 has a width to partially surround the finger (e.g. about the bottom half) and has a length to extend from the proximal phalanx 110 of the finger across the PIP joint 102 to the middle phalanx 112 of the finger without extending across the DIP joint 104. For example, the proximal end of the splint body 106 may be located over a proximal portion of the proximal phalanx 110 and a distal end of the 106 may be located over a distal portion of the middle phalanx 112. For example, the splint body 106 may cover over half of the proximal phalanx 110 and cover over half of the middle phalanx 112.

In the illustrated embodiment, the splint body 106 has an integrally-formed periphery 114, such as by way of example and not limitation a shape similar to the letter "O", defining a central opening 116 of the splint body. The integrally-formed periphery 114 may include a first base 118 configured to partially surround the finger from the palmar side at the proximal phalanx of the finger, a second base 120 configured to partially surround the finger from the palmar side at the middle phalanx of the finger, and opposing sides 122A and 122B that are generally straight extending between the first and second bases 118 and 120 and configured for placement on opposing sides of the finger. The first base 118 has a first end edge 132 and the second base 120 has a second end edge 134. A plane 136 is tangential to the outer surface of the first base 118 from the first end edge 132 to the central opening 116 and tangential to the outer surface of the second base 120 from the central opening 116 to the second end edge 134. When the splint body 106 is applied to the finger, the plane 136 is on the palmar side of the finger and the inner surface of the second base 120 contacts the finger at or near the medial and lateral sides 138 of the middle phalanx. There is a space 140 between the inner surface of the second base 120 and the palmar side of the middle phalanx when a distal interphalangeal joint is in extension.

The straps 108A-108C are configured to wrap around a dorsal side of the finger to secure the splint body 106 to the finger. The straps may include at least a first strap 108A configured for use to wrap around the proximal phalanx of the finger, at least a second strap 108B configured for use to wrap around the middle phalanx of the finger, and at least a third strap 108C attached to and configured for use to wrap around the finger near the PIP joint 102. The straps may be attached to the splint body. For example, the straps may include an adhesive used to permanently attach the straps or an adhesive used to temporarily attach to the straps to the splint body. The adhesive on the straps may be a reusable adhesive enabling the straps to be adhered multiple times to itself or to the splint body. The straps may be completely removable from the splint body such that they be replaced by other straps. The ability to replace old straps with new straps that are clean and dry straps may promote healthy tissue in figure. In some embodiments, the straps do not attach to the splint body, but rather are tightened around the splint body and finger to hold the splint body next to the finger. Thus, the strap may be placed over the finger and splint body, and then tightened and secured to itself to compress the splint body against the finger. Example of such straps may include straps with hook and loop fasteners, straps with adhesives, and zip tie straps. The straps may be perforated or may include apertures to promote breathability.

The straps 108A-108C may include a hook and loop fastener configured and arranged to enable the wrap to be fastened to itself. The straps 108A-108C may include an adhesive to enable the wrap to be fastened to itself or to the splint body. The splint body may include slotted openings configured for use to receive the straps to attach the straps to the splint body. For example, an end of a strap may be fed through a slotted opening along an edge of the splint body, and the end of the strap may be folded over on top of itself and attached via a hook and loop fastener. Athletic tape may be used in place of the straps to hold the splint body to the finger.

According to various embodiments, the splint body is uniformly thick throughout the first base, the second base and the opposing side. The thickness is the same within tolerance. The tolerance may be 25, or 10% or 5% of a nominal value for the thickness. That is, the uniform thickness may be provided as a nominal thickness+/−10%. The thickness of the splint body may be within a range of 0.05 cm to 0.5 cm, or may be within a range of 0.1 cm to 0.3 cm.

For example, the splint body 106 may be formed from a flat sheet of material such as a sheet of metal or thermoplastic material. In an embodiment, a sheet of metal may be cut or stamped to form a flat splint body, and the flat splint body may be pressed against a solid rod to make a partial circle shape for placement around the finger. In an embodiment, a sheet of thermoplastic material may be fed past a rotary die and anvil which may be configured to cut the splint body 106 out of the thermoplastic material. The flat thermoplastic material may then be set into the curved shape to conform to the finger by warming the material to an elevated temperature at which the material becomes moldable, and then cooling. Other methods for manufacturing the splint include, by way of example and not limitation, an injection molding process.

According to various embodiments, the splint body may be configured with a width, extending between side edges 142 to allow the splint to surround between 30% and 70% (e.g., between 108° to 252°), or between 33% and 67% (e.g., between 120° to 240°), or between 40% to 60% (144° to 216°) or between 45% to 55% (162° to 198°) of a periphery of the finger on the palmar side of the finger.

The straps are configured to be manually manipulated by a user when applying the splint. The straps may have a length within a range between 10 cm to 15 cm and a width within a range between 0.3 cm to 1 cm.

The splint body may have a length within a range between 4 cm and 6.5 cm and a width a range between 2 cm to 4 cm. For example, a prototype for an adult male has a length of 5.3 cm and a width of 2.8 cm. The first base and the second base have lengths within a range between 0.7 cm to 2.0 cm, and the central opening may have a length within a range between 2.0 cm to 3.0 cm and a width within a range between 1.5 cm to 2.5 cm. For example, the prototype for an adult male may have a first base with a length of 1.5 cm and a second base with a length of 1.2 cm.

In some embodiments, the central opening is the only opening within the splint body. The central opening may have a length between 2 cm to 3 cm (e.g. 2.5 cm) and a width between 1.5 cm to 2.5 cm (e.g. 2 cm). In some embodiments, the splint body may include ventilation perforations or other vents through which air may contact the tissue. For example, the first and second bases may be perforated or may be fabricated with one or more apertures that form vents to the tissue underlying the splint body. Such perforations or apertures throughout the splint would promote breathability and discourage necrosis.

The above detailed description is intended to be illustrative, and not restrictive. The scope of the disclosure should, therefore, be determined with references to the appended claims, along with the full scope of equivalents to which such claims are entitled.

What is claimed is:
1. A splint for immobilizing a proximal interphalangeal (PIP) joint of a finger in a straight position while allowing both a distal interphalangeal (DIP) joint and a metacarpophalangeal (MCP) joint of the finger to be flexed, the splint comprising:
a splint body having a monolithic structure with opposing first and second ends, the splint body having a size configured to fit the finger and having a non-tapered, partial-cylindrical shape before application to the finger, the splint body being rigid or semi-rigid to maintain a shape of a partial cylinder after application to the finger, wherein the non-tapered, partial-cylindrical shape has a longitudinal axis which, when the splint body is applied to the finger, corresponds to a length direction of the finger with the PIP joint in the straight position, the splint body having a concave side configured to receive the finger from a palmar side of the finger and partially surround the finger from the palmar side of the finger, the splint body having a width, extending between first and second side edges of the splint body along lateral and medial sides of the finger, respectively, to partially surround the finger and having a length to extend from a proximal phalanx of the finger across the PIP joint to a middle phalanx of the finger to maintain the finger straight at the PIP joint, wherein the length does not extend across either the DIP joint or the MCP joint;
the monolithic structure of the splint body having a periphery defining a central opening of the splint body, the periphery of the monolithic structure including:
a first base having a first end edge at the first end of the splint body and configured to partially surround the finger from the palmar side at the proximal phalanx of the finger without extending across the MCP joint;
a second base having a second end edge at the second end of the splint body and configured to partially surround the finger from the palmar side at the middle phalanx of the finger without extending across the DIP joint; and
opposing sides, including the first and second edges of the splint body, that extend between the first and second bases and are configured for placement on opposing lateral and medial sides of the finger to maintain the finger straight at the PIP joint, wherein the first base, the second base and the opposing sides of the monolithic structure provide the non-tapered, partial cylindrical shape of the splint body, and both the first base and the second base having a cross section, taken perpendicular to the longitudinal axis, in a shape of a partial circle, wherein the splint body is uniformly thick throughout the first base, the second base and the opposing sides, and the splint body has an inner surface, on the concave side, equidistant from the longitudinal axis and has an outer surface equidistant from the longitudinal axis and to provide the non-tapered, partial cylindrical shape, wherein a plane parallel to the longitudinal axis is tangential to the outer surface of the first base from the first end edge to the central opening and tangential to the outer surface of the second base from the central opening to the second end edge, and wherein when the splint body is applied to the finger the plane is on the palmar side of the finger and the inner surface of the second base in the shape of the partial circle contacts the finger at or near the medial and lateral sides of the middle phalanx and is spaced from the palmar side of the middle phalanx at the second end edge when the distal interphalangeal joint is in extension and the first and second bases are not turned on the proximal and middle phalanx, respectively; and straps configured to wrap around a dorsal side of the finger to secure the splint body to the finger, the straps including:
at least a first strap attached to the first base and configured for use to wrap around the proximal phalanx of the finger without wrapping around the MCP joint;
at least a second strap attached to the second base and configured for use to wrap around the middle phalanx of the finger without wrapping around the DIP joint; and
at least a third strap attached to at least one of the opposing sides between the first base and the second base, and configured for use to wrap around the finger.

2. The splint of claim 1, wherein each of the first strap, the second strap, and the third strap includes an adhesive to enable each of the first strap, the second strap, and the third strap to be fastened to itself or to the splint body.

3. The splint of claim 2, wherein the adhesive on the first, second and third straps is a reusable adhesive enabling the straps to be adhered multiple times to itself or to the splint body.

4. The splint of claim 2, wherein the first, second and third straps are configured to be replaceable straps.

5. The splint of claim 1, wherein a thickness of the splint body is within a range of 0.05 to 0.5 cm.

6. The splint of claim 5, wherein the thickness of the splint body is within a range of 0.1 to 0.3 cm.

7. The splint of claim 1, wherein the third strap is configured for use to wrap around the finger at the PIP joint and the first strap is configured for use to wrap around a proximal portion of the proximal phalanx of the finger.

8. The splint of claim 1, wherein the first base, the second base and the opposing sides of the monolithic structure provide the non-tapered, partial cylindrical shape of the splint body, and both the first base and the second base are configured to surround between 40% to 60% of a periphery of the finger from the palmar side of the finger to allow the rigid or semi-rigid splint body to be applied to the finger while the PIP joint of the finger remains in the straight position and removed from the finger while the PIP joint of the finger remains in the straight position, wherein the first strap is configured to wrap around the first base of the splint body, the second strap is configured wrap around the second base of the splint body, and the third strap is configured to wrap around the opposing sides of the splint body that extend between the first and second bases.

9. The splint of claim 1, wherein each of the first strap, the second strap, and the third strap includes a hook and loop fastener configured and arranged to enable each of the first strap, the second strap and the third strap to be fastened to itself.

10. The splint of claim 1, wherein the first strap, the second strap, and the third strap are attached to the splint body using an adhesive.

11. The splint of claim 1, wherein the splint body includes slotted openings configured for use to receive the first, second and third straps to attach the first, second and third straps to the splint body.

12. The splint of claim 1, wherein the straps have a length within a range between 10 cm to 15 cm and a width within a range between 0.3 cm to 1 cm.

13. The splint of claim 1, wherein the splint body has a length within a range between 4 cm and 6.5 cm and within a width a range between 2 cm to 4 cm, wherein the first base and the second base have lengths within a range between 0.7 cm to 2.0 cm, and wherein the central opening has a length within a range between 2.0 cm to 3.0 cm and a width within a range between 1.5 cm to 2.5 cm.

14. The splint of claim 1, wherein the splint body includes ventilation perforations.

15. The splint of claim 1, wherein the splint body being fabricated from a material having a shape memory.

16. The splint of claim 1, wherein the splint body is formed from a material comprising thermoplastic.

17. The splint of claim 1, wherein the splint body is formed from a material comprising a metal or metal alloy.

18. A method for immobilizing a proximal interphalangeal (PIP) joint of a finger om a straight position while allowing both a distal interphalangeal (DIP) joint and a metacarpophalangeal (MCP) joint of the finger to be flexed, comprising:
attaching a splint to a finger, the splint including a splint body having opposing first and second ends and a monolithic structure and having a size configured to fit the finger and straps, the splint body having a non-tapered, partial-cylindrical shape extending before the first and second ends before application to the finger, the splint body being rigid or semi-rigid to maintain a shape of a partial cylinder after application to the finger, wherein the non-tapered, partial-cylindrical shape has a longitudinal axis which, when the splint body is applied to the finger, corresponds to a length direction of the finger with the PIP joint in the straight position, the splint body having a concave side to receive the finger from a palmar side of the finger and partially surround the finger from the palmar side of the finger, the splint body having a width, extending between first and second side edges of the splint body along lateral and medial sides of the finger, respectively, to partially surround the finger and having a length to extend from a proximal phalanx of the finger across the PIP joint to a middle phalanx of the finger to maintain the finger straight at the PIP joint without extending across either the distal interphalangeal (DIP) joint or the MCP joint, the monolithic structure of the splint body having a periphery defining a central opening of the splint body, the periphery of the monolithic structure including a first base having a first end edge at the first end of the splint body and configured to partially surround the finger from the palmar side at the proximal phalanx of the finger without extending across the MCP joint, a second base having a second end edge at the second end of the splint body and configured to partially surround the finger from the palmar side at the middle phalanx of the finger without extending across the DIP joint, and opposing sides, including the first and second edges of the splint body, that extend between the first and second bases and are configured for placement on opposing lateral and medial sides of the finger to maintain the finger straight at the PIP joint, wherein the first base, the second base and the opposing sides of the monolithic structure provide the non-tapered, partial cylindrical shape of the splint body, and both the first base, the second base having a cross section, taken perpendicular to the longitudinal axis, in a shape of a partial circle, wherein the splint body is uniformly thick throughout the first base, and the second base and the opposing sides, and the splint body has an inner surface, on the concave side, equidistant from the longitudinal axis and has an outer surface equidistant from the longitudinal axis and to provide the non-tapered, partial cylindrical shape, wherein a plane parallel to the longitudinal axis is tangential to the outer surface of the first base from the first end edge to the central opening and tangential to the outer surface of the second base from the central opening to the second end edge, and wherein when the splint body is applied to the finger the plane is on the palmar side of the finger and the inner surface of the second base in the shape of the partial circle contacts the finger at er near the medial and lateral sides of the middle phalanx and is spaced from the palmar side of the middle phalanx at the second end edge when the distal interphalangeal joint is in extension and the first and second bases are not turned on the proximal and middle phalanx, respectively, wherein attaching the splint to the finger includes wrapping at least a first strap attached to the first base around the proximal phalanx of the finger without wrapping around the MCP joint, wrapping at least a second strap attached to the second base around the middle phalanx of the finger without wrapping around the DIP joint, and wrapping at least a third strap attached to at least one of the opposing sides around the finger.

19. The method of claim 18, wherein the method is used in a method for treating PIP injuries, the method further comprising instructing a patient to flex the DIP joint of the finger when the splint body is attached to the finger.

\* \* \* \* \*